(12) United States Patent
Al-Abed (10) Patent No.: US 8,742,173 B2
(45) Date of Patent: Jun. 3, 2014

(54) PHENOLIC HYDRAZONE MACROPHAGE MIGRATION INHIBITORY FACTOR INHIBITORS

(75) Inventor: Yousef Al-Abed, Locust Valley, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 13/418,877

(22) Filed: Mar. 13, 2012

(65) Prior Publication Data

US 2012/0178805 A1    Jul. 12, 2012

Related U.S. Application Data

(62) Division of application No. 12/225,572, filed as application No. PCT/US2007/007277 on Mar. 23, 2007, now Pat. No. 8,193,247.

(60) Provisional application No. 60/785,834, filed on Mar. 24, 2006.

(51) Int. Cl.
*C07C 251/86* (2006.01)

(52) U.S. Cl.
CPC .................................... *C07C 251/86* (2013.01)
USPC ........................................................ 564/251

(58) Field of Classification Search
CPC ........................... C07C 251/86; C07C 251/72
USPC .................................................. 564/251, 250
See application file for complete search history.

(56) References Cited

U.S. PATENT DOCUMENTS

| | | | |
|---|---|---|---|
| 5,728,646 | A | 3/1998 | Tominaga et al. |
| 5,753,652 | A | 5/1998 | Fassler et al. |
| 6,503,914 | B1 | 1/2003 | Benish et al. |
| 2003/0008908 | A1 | 1/2003 | Al-Abed |
| 2003/0099653 | A1 | 5/2003 | Bucala et al. |
| 2005/0239740 | A1 | 10/2005 | Verkman et al. |
| 2006/0004002 | A1 | 1/2006 | Thrash et al. |
| 2006/0178527 | A1* | 8/2006 | Kelly et al. .......... 562/439 |

FOREIGN PATENT DOCUMENTS

| | | |
|---|---|---|
| CA | 2542106 | 4/2005 |
| DE | 10346913 | 5/2005 |
| EP | 0839669 | 5/1998 |
| EP | 1612204 | 1/2004 |
| JP | 58189192 A | 11/1983 |
| WO | 0147923 A1 | 7/2001 |
| WO | WO2004009596 | 1/2004 |
| WO | WO2004009602 | 1/2004 |
| WO | WO2005037773 | 4/2005 |
| WO | WO2005037779 | 4/2005 |
| WO | 2005084651 | 9/2005 |
| WO | WO2005084651 | 9/2005 |
| WO | 2006014404 A1 | 2/2006 |
| WO | WO2006086517 | 8/2006 |

OTHER PUBLICATIONS

STN search abstract (Barnes et al., Journal of the Chemical Society: 2824-33, 1950).*
Preliminary Notice of Reasons for Rejection dated Jul. 25, 2012 in corresponding Japanese Application No. 2009-501581 with English translation.
Chemical Abstracts, 1981, vol. 94, No. 13, p. 704, Abstract No. 102973c.
Chemical Abstracts, 1981, vol. 95, No. 5, p. 711, Abstract No. 42566f.
Wiley, et al., "Methyl and Dimethylhydrazones," Journal of Organic Chemistry (1959), vol. 24, pp. 1925-1928.
Johnson, et al., "Bisaryloxime Ethers as Potent Inhibitors of Transthyretin Amyloid Fibil Formation," Journal of Medical Chemistry (2005), pp. 1576-1587.
Database CA (Online), Chemical Abstracts Service, Columbus, OH, Gabrielyan, et al., "Effect of Eicosanoids on the Accumulation of Cholesterol and Proliferation of Subendothelial Cells of Human Aorta," retrieved from STN Database Accession No. 1988:449078, and Byulleten Eksperimental Noi Biologii Meditsiny, 105(1), 35-7 Coden Bebmae ISSN: 0365-9615 (1998).
Office Action for the corresponding European Application No. 07753868.4-2117, dated Jul. 27, 2009.
Office Action for the corresponding European Application No. 07753868.4-2117, dated Sep. 7, 2010.
Supplementary Partial European Search Report for European Application No. EP07753868.
Zverev, et al., "Basicity and steric structure of some hydrazones," Abstract, RN 14(4), 1978.
Buu-Hoi, et al., "Some new tuberculostatic thiosemicarbazones," J. Organic Chemistry, 18 (1953), pp. 121-126.
Justus Liebig, Annalen Der Chemie, 321 (1902), pp. 1-32.
Rabjohn, et al., "Carbazic acid esters as carbonyl reagents," J. Am. Chem. Soc. 75:9 (1953), pp. 2259-2261.

(Continued)

*Primary Examiner* — Bong-Sook Baek
(74) *Attorney, Agent, or Firm* — Amster, Rothstein & Ebenstein LLP (57) ABSTRACT

Provided are various compounds of Formula (I): Also provided are pharmaceutical compositions comprising the above compounds. Additionally, methods of inhibiting macrophage migration inhibitory factor (MIF) activity in a mammal are provided, as are methods of treating or preventing inflammation in a mammal. Further provided are methods of treating a mammal having sepsis, septicemia, and/or endotoxic shock. Also provided are methods of treating a mammal having an autoimmune disease, and methods of treating a mammal having a tumor.

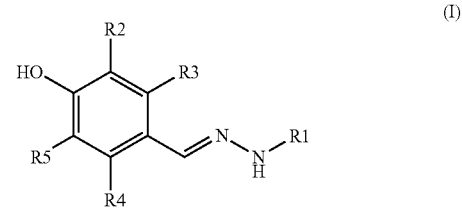

(I)

11 Claims, 7 Drawing Sheets

(56) References Cited

OTHER PUBLICATIONS

Barnes, et al., "The synthesis of thyroxine and related substances, Part VII, The preparation of dipenyl ethers from 2:6-di-iodophenols," J. Chem. Soc. (1950), pp. 2824-2833.
Ferguson, et al., "Some new fluorinated phenolic aldehydes and acids," J. Am. Chem. Soc. 68 (1946), pp. 2502-2504.
Katz et al., "Hydrazine derivatives. I. Benzalthio-and bisbenzaldithio-salicylhydrazides," J.Org. Chem. 18 (1953), pp. 1380-1402.
Calabretta, et al., "Peptidyl and azapeptidyl methylketones as substrate analog inhibitors of papain and cathepsin B," Eur. J. Med. Chem. 30 (1995), pp. 931-941.
Ghabrial et al., "Reactions with maleimides: synthesis of several new fused pyrazolidines, delta 2-pyrazoline and pyrazole derivatives," Heterocycles, 23:5 (1985), pp. 1161-1166.
Ramanathan et al., "Analogs of tuberin: syntheses and biological activity of some new 4-methoxy styryl carbamates and 4-methoxy styryl semicarbazones," J. Indian Chem. Soc. LV (1978), pp. 1036-1039.
Abstract: "Hydrazinecarboxylic acid, 2-[4-hydroxyphenyl) methylene]-, [4-methoxphenyl) methyl ester (9CI)," Database Registry (2004).
He XF, et al, "The synthesis and antineoplastic activity of substituted benzaldehyde arysulfonylhydrazones," J. West China Univ. Med. Sci. 19:3 (1988), pp. 317-319.
Sen, et al., "Studies on riemer-tiemann reaction," J. Indian Chem. Soc., vol. 9 (1932), pp. 173-179.
International Search Report for PCT Application No. PCT/US2007/007277, (2008).
Written Opinion of the International Searching Authority for PCT Application No. PCT/US2007/007277, (2008).
Office Action for U.S. Appl. No. 12/225,572, dated Dec. 9, 2010.
Office Action for U.S. Appl. No. 12/225,572, dated Sep. 13, 2011.
Office Action for U.S. Appl. No. 12/225,572, dated Sep. 29, 2010.
Official Decision of Final Rejection dated Mar. 16, 2013 in connection with Japanese Patent Application No. 2009-501581, 5 pages, and an English Translation, 5 pages.
Registry (STN) [online], Apr. 22, 2005, CAS Registry Nos. 849049-62-3; Registry (STN) [online], Apr. 22, 2005, CAS Registry Nos. 849049-61-2; Registry (STN) [online], Mar. 25, 2002, CAS Registry Nos. 402768-06-3; Registry (STN) [online], Dec. 14, 2001, CAS Registry Nos. 375359-05-0; Registry (STN) [online], Jun. 11, 2001, CAS Registry Nos. 340306-43-6; Registry (STN) [online], Nov. 3, 2000, CAS Registry Nos. 301203-43.0; Registry (STN) [online], Nov. 16, 1984, CAS Registry Nos. 57699-48-6.
Registry (STN) [online], Nov. 16, 1984, CAS Registry Nos. 16435-05-05; Registry (STN) [online], Nov. 16, 1984, CAS Registry Nos. 365-30-0; (5 pages).
Patent Examination Report No. 3 received by the Australian Government dated Feb. 26, 2013 in connection with Australian Patent Application No. 2007231012, 3 pages.
Chemical Abstract CAS R.N. 674349-50-9, Apr. 12, 2004, 1 page.
Chemical Abstract STN Registry R.N. 381695-24-5, dated Jan. 10, 2002, cited in Oct. 22, 2013 Office Action in corresponding Japanese Application No. 2009-501581, 1 page.
Chemical Abstract STN Registry R.N. 357919-66-3, dated Sep. 21, 2001, cited in Oct. 22, 2013 Office Action in corresponding Japanese Application No. 2009-501581, 1 page.

\* cited by examiner

PHENOLIC HYDRAZONE MACROPHAGE MIGRATION INHIBITORY FACTOR INHIBITORS

CROSS-REFERENCE TO RELATED APPLICATION

This application is a divisional of U.S. Ser. No. 12/225,572 filed Dec. 5, 2008, now U.S. Pat. No. 8,193,247, a U.S. National Phase of PCT Application No. PCT/US2007/007277, filed Mar. 23, 2007, now allowed, which claims the benefit of U.S. Provisional Application No. 60/785,834, filed Mar. 24, 2006.

BACKGROUND OF THE INVENTION (1) Field of the Invention

The present invention relates to cytokine inhibitors. More specifically, the present invention identifies and characterizes several inhibitors of macrophage migration inhibitory factor.

(2) Description of the Related Art

Macrophage migration inhibitory factor (MIF) is a potent pro-inflammatory cytokine, critically involved in the pathogenesis of sepsis and other inflammatory disorders (Calandra and Roger, 2003; Riedemann et al., 2003). Sepsis, a lethal systemic inflammatory reaction to infection, kills more than 215,000 people per annum in the US alone. There is currently no anti-inflammatory therapeutic agent that is approved by the FDA, for its clinical management. MIF has been demonstrated to be an important late-acting mediator of systemic inflammation, and inhibiting its activity in vivo attenuates the lethal consequences of endotoxemia and sepsis in rodents (Calandra et al., 2000; Al-Abed et al., 2005).

MIF exists as a homotrimer (Sugimoto et al., 1995; Sun et al., 1996; Suzuki et al., 1996; Taylor et al., 1999) with the unique ability to catalyze the tautomerization of non-physiological substrates such as D-dopachrome and L-dopachrome methyl ester into their respective indole derivatives (Rosengren et al., 1996). While the physiological role of the tautomerase activity is uncertain, compounds that are structurally similar to D- and L-dopachrome can bind to and thereby block the MIF's tautomerase active site (Al-Abed et al., 2005; Cios et al., 2002; Cheng and Al-Abed, 2006; Lubetsky et al., 2002; Senter et al., 2002). N-acetyl-p-benzoquinone imine (NAPQI) forms a covalent complex with MIF at its active site (FIG. 1) and is capable of irreversibly inhibiting the adverse biological effect of MIF (Senter et al., 2002). However, the toxicity of NAPQI precludes its use as a viable clinical inhibitor of MIF.

Based on the above, the development of non-toxic small molecule inhibitors of MIF activity warrants further investigation.

SUMMARY OF THE INVENTION

The inventor has identified and characterized several new compounds that inhibit MIF activity.

The present invention is thus directed to compounds of Formula I:

I where R1 is an alkyl, a substituted alkyl, a cycloalkyl, a substituted cycloalkyl, a heterocyclic group, a substituted heterocyclic group, an aryl, a substituted aryl, a heteroaryl, a substituted heteroaryl, a hydroxy, an alkoxy, an aryloxy, an oxo, an amino, a halogen, a formyl, an acyl, a carboxy, a carboxyalkyl, a carboxyaryl, an amido, a carbamoyl, a guanidino, a ureido, an amidino, a mercapto, a sulfinyl, a sulfonyl or a sulfonamide, and R2, R3, R4 and R5 are independently a halogen, —OH, —SH, —NH$_2$, —NO$_2$, —OR6, or H, where R6 is a straight or branched C$_1$-C$_6$ alkyl.

The invention is also directed to pharmaceutical compositions comprising any of the above compounds, or a pharmaceutically acceptable salt thereof, in a pharmaceutically acceptable carrier.

The present invention is additionally directed to methods of inhibiting macrophage migration inhibitory factor (MIF) activity in a mammal. The methods comprise administering the above pharmaceutical composition to the mammal in an amount effective to inhibit MIF activity in the mammal.

Further, the invention is directed to methods of treating or preventing inflammation in a mammal. The methods comprise administering the above pharmaceutical composition to the mammal in an amount effective to treat or prevent the inflammation in the mammal.

Also, the present invention is directed to methods of treating a mammal having sepsis, septicemia, and/or endotoxic shock. The methods comprise administering the above pharmaceutical composition to the mammal in an amount effective to treat the sepsis, septicemia and/or endotoxic shock.

The invention is further directed to methods of treating a mammal having an autoimmune disease. The methods comprise administering the above pharmaceutical composition to the mammal in an amount effective to treat the autoimmune disease.

Additionally, the present invention is directed to methods of treating a mammal having a tumor, the method comprising administering the above pharmaceutical composition to the mammal in an amount effective to treat the tumor.

DETAILED DESCRIPTION OF THE INVENTION

The present invention provides several new compounds that inhibit MIF activity. See Examples.

The present invention is thus directed to compounds of Formula I:

where R1 is an alkyl, a substituted alkyl, a cycloalkyl, a substituted cycloalkyl, a heterocyclic group, a substituted heterocyclic group, an aryl, a substituted aryl, a heteroaryl, a substituted heteroaryl, a hydroxy, an alkoxy, an aryloxy, an oxo, an amino, a halogen, a formyl, an acyl, a carboxy, a carboxyalkyl, a carboxyaryl, an amido, a carbamoyl, a guanidino, a ureido, an amidino, a mercapto, a sulfinyl, a sulfonyl or a sulfonamide, and R2, R3, R4 and R5 are independently a halogen, —OH, —SH, —NH$_2$, —NO$_2$, —OR6, or H, where R6 is a straight or branched C$_1$-C$_6$ alkyl.

Preferably, only one of R2, R3, R4 and R5 is not an H. Also preferably, R2 is fluorine or H. More preferably, only R2 is not an H. Even more preferably, R2 is a halogen and R3, R4 and R5 are all H. Most preferably, R2 is fluorine and R3, R4 and R5 are all H.

For any of the above compounds, R1 is preferably COOMe, COOEt, COOtBu, COOCH$_2$Ph, COOCH$_2$PhOMe, COPh, SO$_2$Ph, Me, Ph, PhOMe, COOtBu, Ph, or PhOMe, where Me is CH$_3$, Ph is a phenyl, and Bu is a butyl. More preferably, R1 is COOtBu, Ph, or PhOMe. Even more preferably, the compound is any one of compounds 4-9 and 11-19 of Tables 1 and 2. Most preferably, the compound is any one of compounds 5, 6, 7, 8, 9, or 19 of Table 1 or 13, 14, 15, or 18 of Table 2. In some aspects, the compound is compound 5 of Table 1. In other aspects, the compound is compound 6 of Table 1. In still other aspects, the compound is compound 7 of Table 1. In additional aspects, the compound is compound 8 of Table 1. In further aspects, the compound is compound 9 of Table 1. Also, the compound can be compound 19 of Table 1. The compound can also be compound 13 of Table 2. Additionally, the compound can be compound 14 of Table 2. The compound can further be compound 15 of Table 2. The compound can additionally be compound 18 of Table 2.

The invention is also directed to pharmaceutical compositions comprising any of the above compounds, or a pharmaceutically acceptable salt thereof, in a pharmaceutically acceptable carrier.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The compounds can also be prepared for nasal administration. As used herein, nasal administration includes administering the compound to the mucous membranes of the nasal passage or nasal cavity of the patient. Pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

The compounds of the invention may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group.

The present invention is additionally directed to methods of inhibiting macrophage migration inhibitory factor (MIF) activity in a mammal. The methods comprise administering any of the above pharmaceutical compositions to the mammal in an amount effective to inhibit MIF activity in the mammal.

These methods can be used on any mammal. Preferably, the mammal is a human. It is also preferred that the mammal has or is at risk for a condition that comprises an inflammatory cytokine cascade that is at least partially mediated by an MIF. Non-limiting examples of such conditions include proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome and Hodgkins disease. A preferred such condition is sepsis, septicemia, and/or endotoxic shock.

MIF has been shown to play an important role in autoimmune disease. See, e.g., Cvetjovic et al., 2005. The present methods would thus be useful in treatment of autoimmune disease. Thus, in some aspect of these methods, the mammal has or is at risk for an autoimmune disease. Non-limiting examples of such autoimmune diseases are multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome and autoimmune inflammatory eye disease.

MIF also is known to promote tumor invasion and metastasis. See, e.g., Sun et al., 2005. The present methods would therefore be useful for treatment of a mammal that has a tumor.

The invention is also directed to methods of treating or preventing inflammation in a mammal. The methods comprise administering the above pharmaceutical composition to the mammal in an amount effective to treat or prevent the inflammation in the mammal.

For these methods, the mammal is preferably a human. The mammal can have, or be at risk for, a disease involving inflammation, for example proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type I diabetes, type 2 diabetes, Berger's disease, Retier's syndrome, or Hodgkins disease. Preferably, the mammal has sepsis, septicemia, and/or endotoxic shock, or is at risk for sepsis, septicemia, and/or endotoxic shock.

These methods can include the administration of a second anti-inflammatory agent to the mammal. Examples of such second anti-inflammatory agents are NSAIDs, salicylates, COX inhibitors, COX-2 inhibitors, and steroids. Preferably, the mammal has or is at risk for sepsis, septicemia, and/or endotoxic shock and the second treatment is administration of a muscarinic agonist, an adrenomedullin, an adrenomedullin binding protein, a milk fat globule epidermal growth factor VIII, an activated protein C, or an α2A-adrenergic antagonist.

The present invention is also directed to methods of treating a mammal having sepsis, septicemia, and/or endotoxic shock. The methods comprise administering the above pharmaceutical composition to the mammal in an amount effective to treat the sepsis, septicemia and/or endotoxic shock.

The invention is further directed to methods of treating a mammal having an autoimmune disease. The methods comprise administering the above pharmaceutical composition to the mammal in an amount effective to treat the autoimmune disease. Examples of such autoimmune diseases include multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome and autoimmune inflammatory eye disease.

Additionally, the present invention is directed to methods of treating a mammal having a tumor, the method comprising administering the above pharmaceutical composition to the mammal in an amount effective to treat the tumor.

As established in Example 2 below, these compounds can be effectively administered orally. Thus, in any of the above methods, the pharmaceutical composition can be administered orally. Alternatively, the pharmaceutical composition can be administered parenterally.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Phenolic Hydrazones are Potent Inhibitors of Macrophage Migration Inhibitory Factor Proinflammatory Activity and are Survival-Improving Agents in Sepsis Example Summary A series of phenolic hydrazones were synthesized and evaluated for their inhibition of MIF activity. Compound 7 emerged as a potent inhibitor of MIF tautomerase with an $IC_{50}$ of 130 nM. Compound 7 dose-dependently suppressed TNFα secretion from lipopolysaccharide-stimulated macrophages. The therapeutic importance of the MIF inhibition by compound 7 is demonstrated by the significant protection from the lethality of sepsis when administration of the compound was initiated in a clinically relevant time frame.

Introduction

Figure 1:
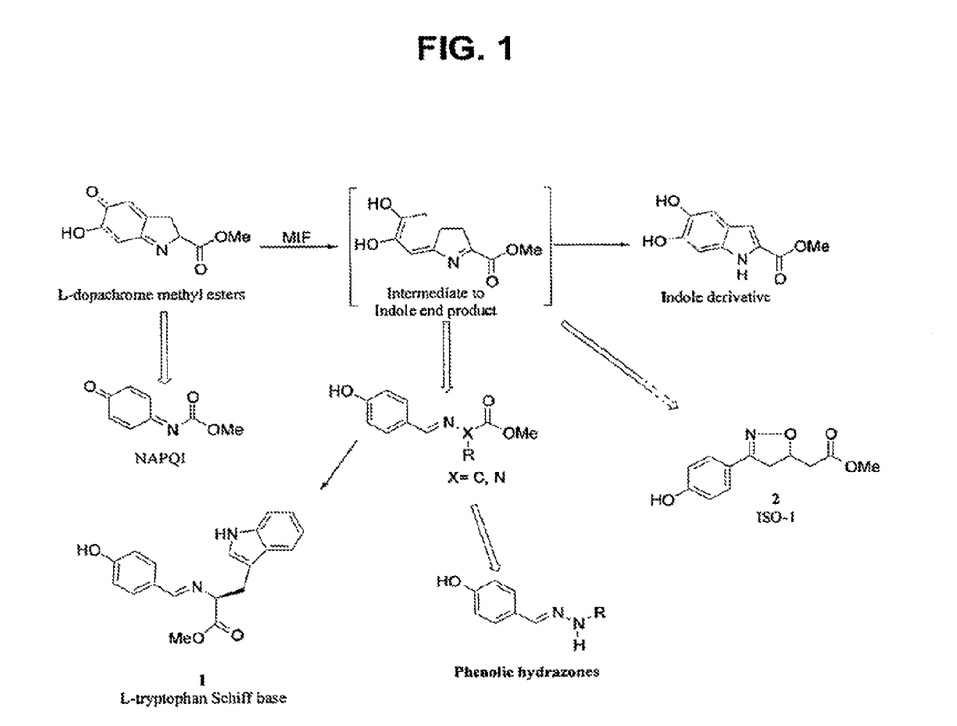
FIG. 1 is a diagram showing a scheme for the rational design of MIF inhibitors.

A rational design approach was used to produce a more potent, small molecule inhibitor of MIF. The indole intermediate of MIF tautomerase catalysis presented itself as a suitable template for the development of potential MIF inhibitors. It was reasoned that compounds designed around the phenyl imine scaffold could act as potential MIF antagonists. Indeed, from this rational design the amino acid Schiff bases and the isoxazoline compounds as MIF tautomerase inhibitors were developed (Dios et al., 2002; Lubetsky et al., 2002). Among the amino acid Schiff bases tested for their ability to inhibit the tautomerase activity of MIF, it was found that compound 1 was the most potent (FIG. 1, Table 1). Recently, an isoxazoline inhibitor of MIF, "ISO-1" (compound 2, FIG. 1) was reported, which blocks the tautomerase site, inhibits the ability of MIF to overcome anti-inflammatory glucocorticoid activities in vitro and improves survival in animal models of experimental sepsis (Lubetsky et al., 2002).

To find more potent inhibitors of MIF, the phenyl imine scaffold was revisited and modified by adding nitrogen to afford hydrazone-type compounds (FIG. 1). Previous studies on the amino acid Schiff bases and compound 2 revealed that a para-hydroxyl group, as exemplified by a phenolic moiety, is a key structural feature and is required for activity. Replacing the phenolic moieties of 1 and 2 with either phenyl- or halide-substituted phenyl or p-methoxyphenyl groups resulted in the decrease or complete loss of their ability to inhibit MIF tautomerase activity (Dios et al., 2002; Lubetsky et al., 2002). In accordance with this result, the chemical structure of the new pharmacophores must contain a phenolic ring (FIG. 1). Utilizing this key structural feature and the observations of 1 and 2 complexed with MIF, phenolic hydrazones 3-19 (Tables 1 and 2) were synthesized as potential MIF inhibitors.

TABLE 1

Phenolic hydrazones and $IC_{50}$ values for inhibition of MIF tautomerase activity.

| Compounds[a] | Ar | R | $IC_{50}$ $(\mu M)^{b}$ |
|---|---|---|---|
| 1 L-tryptophan Schiff base | | | 1.6 |
| 2 ISO-1 | | | 7 |
| 3 |  | H | >500 |
| 4 |  | CH$_3$ | 43 |
| 5 |  |  | 2.6 |

TABLE 1-continued

Phenolic hydrazones and IC$_{50}$ values for inhibition of MIF tautomerase activity.

| Compounds[a] | Ar | R | IC$_{50}$ (μM)[b] |
|---|---|---|---|
| 6[c] | 4-HO-C$_6$H$_4$- | 4-MeO-C$_6$H$_4$- | 0.48 |
| 7[c] | 3-F-4-HO-C$_6$H$_3$- | 4-MeO-C$_6$H$_4$- | 0.13 |
| 8[c] | 3-Cl-4-HO-C$_6$H$_3$- | 4-MeO-C$_6$H$_4$- | 0.22 |
| 9[c] | 3-Br-4-HO-C$_6$H$_3$- | 4-MeO-C$_6$H$_4$- | 0.33 |
| 16 | 4-HO-C$_6$H$_4$- | COPh | 36.5 |
| 17 | 4-HO-C$_6$H$_4$- | SO$_2$Ph | 86 |
| 19 | 3-F-4-HO-C$_6$H$_3$- | Ph | 1.5 |

[a]Compounds were characterized by $^1$H, $^{13}$C NMR and MS.
[b]Spectrophotometric analysis of MIF tautomerase activity on L-dopachrome methyl ester (see experimental).
[c]See experimental for general procedure for the synthesis of 6-9.

TABLE 2

Phenolic hydrazone carbamates and IC$_{50}$ values for inhibition of MIF tautomerase activity.

| Compounds[a] | Ar | R' | IC$_{50}$ (μM)[b] |
|---|---|---|---|
| 11 | 4-HO-C$_6$H$_4$- | CH$_3$ | 55 |
| 12 | 4-HO-C$_6$H$_4$- | CH$_2$CH$_3$ | 43 |
| 13 | 4-HO-C$_6$H$_4$- | C(CH$_3$)$_3$ | 5.5 |
| 14 | 4-HO-C$_6$H$_4$- | CH$_2$Ph | 10 |
| 15 | 4-HO-C$_6$H$_4$- | CH$_2$-C$_6$H$_4$-4-OMe | 8 |
| 18 | 3-F-4-HO-C$_6$H$_3$- | C(CH$_3$)$_3$ | 2.4 |

[a]Compounds were characterized by $^1$H, $^{13}$C NMR and MS (see supporting information).
[b]Spectrophotometric analysis of MIF tautomerase activity on L-dopachrome methyl ester.

All of the hydrazones prepared in this study, compounds 3-19, have one common key structural feature, in that they all possess a "phenolic head" in the form of a 4-hydroxyphenyl ring. It has been shown that the phenolic ring forms key hydrogen bond interactions between the amino acid residue asparagine-97C of the hydrophobic surface within the MIF active site (Dios et al., 2002; Lubetsky et al., 2002; Orita et al., 2001). In addition to this important hydrogen bond interaction, there is a hydrophobic interaction that exists between the aromatic ring of the phenol and the side chains of the amino acid residues, Pro-1, Met-2, Ile-64, Tyr-95, Val-106 and Phe-113, of the hydrophobic pocket, that further contributes to the binding of the inhibitor (Orita et al., 2001). Supporting evidence for the key interaction between the hydroxyl functionality and the amino acid residue asparagine-97C was obtained by 1) modifying its position and 2) replacing the hydroxyl group with other functional groups. The position of the hydroxyl group is a critical feature of the hydrazones in that changing its position from para ($IC_{50}$ 2.5 µM) to meta ($IC_{50}$ 150 µM) resulted in a dramatic loss of its ability to inhibit MIF tautomerase activity. Furthermore, replacing the hydroxyl group with hydrogen, fluoro, amino, methoxy and nitro functionalities afforded hydrazones that were inactive (data not shown). In developing a structure-activity relationship between the phenolic hydrazones and MIF, hydrazones 3-6 were synthesized from the simple hydrazine, methyl hydrazine, phenyl hydrazine and p-methoxyphenyl hydrazine. One further prerequisite for activity of our phenolic hydrazones is that they require a hydrophobic tail. This is evident from compound 3 ($IC_{50}$=>500 µM). The hydrogen substituent of the hydrazone in this compound does not offer any hydrophobic interactions and as a result is a very poor inhibitor of MIF tautomerase activity (Table 1). Upon replacing the hydrogen with a methyl group, a pronounced improvement in the ability of the methyl hydrazone 4 to inhibit the tautomerase activity of MIF ($IC_{50}$=43 µM) was observed. This suggests that there is a hydrophobic interaction between the methyl group and the surface of MIF. Replacing the methyl group of 4 with the more hydrophobic phenyl ring affords the hydrazone 5 ($IC_{50}$=2.6 µM) that is 16 times more potent. Installation of a para-methoxy group on the aromatic ring of 5, gives hydrazone 6 that is 5-fold more potent as an inhibitor than the parent compound. This increased binding of the p-methoxy phenyl hydrazone may be explained by hydrogen bond interactions between the ether oxygen and the known amino acid residues, and the possibility of pi-pi stacking and/or van der Waals interactions between the p-methoxy phenyl ring and the second hydrophobic region of the MIF active site. It has been reported that the amino acids, Pro-33, Tyr-36, Phe-49, Trp-108, and Phe-113, make up the second hydrophobic surface at the rim of the active site of MIF (Dios et al., 2002; Orita et al., 2001). These residues further contribute to the hydrophobic and hydrogen bond interactions between the pharmacophore and the active site of MIF (Orita et al., 2001). In further support of these interactions, it was previously shown that the L-amino acid Schiff bases inhibitory effect was improved by five-fold upon changing the amino acid residue from L-phenylalanine ($IC_{50}$=50 µM) to L-tyrosine ($IC_{50}$=10 µM), respectively. This suggests that the increased potency was attributed to a hydrogen bond interaction within residues at the rim of MIF (Dios et al., 2002). Hydrazone 6 is twelve times more potent an inhibitor than L-tryptophan Schiff base 1, so far the most potent inhibitor of MIF described in the literature (Al-Abed et al., 2005; Dios et al., 2002; Cheng and Al-Abed, 2006; Orita et al., 2001; Orita et al., 2002). Recently, it was discovered that mono-fluorination of 2 improved the inhibition of MIF activity (Cheng and Al-Abed, 2006). As a consequence, we synthesized the 3-fluoro, 3-chloro, and 3-bromo-4-hydroxyphenyl derivatives of the more potent hydrazone, namely the p-methoxyphenyl hydrazine (6). The synthesis of the mono-halogenated hydrazone derivatives involved treatment of a suspension of the 4-methoxyphenylhydrazine hydrochloride and the 3-halogenated-4-hydroxybenzaldehyde in methanol with aqueous sodium hydroxide (Table 1). A general increase in the inhibition of the MIF tautomerase activity was observed for the 3-halogenated-4-hydroxyphenyl hydrazone derivatives 7-9 (Table 1). Among these hydrazones, compound 7 showed the most potent inhibition with an $IC_{50}$ value of 130 nM, whilst 8 and 9 gave values of 220 nM and 330 nM, respectively. The significant improvement in the inhibitory effect of these halogenated hydrazones 7-9 may be explained by the inductive effect that may lead to changes in the polarization of the hydroxyl moiety thereby making it a stronger hydrogen bond donor/acceptor.

Figure 2:
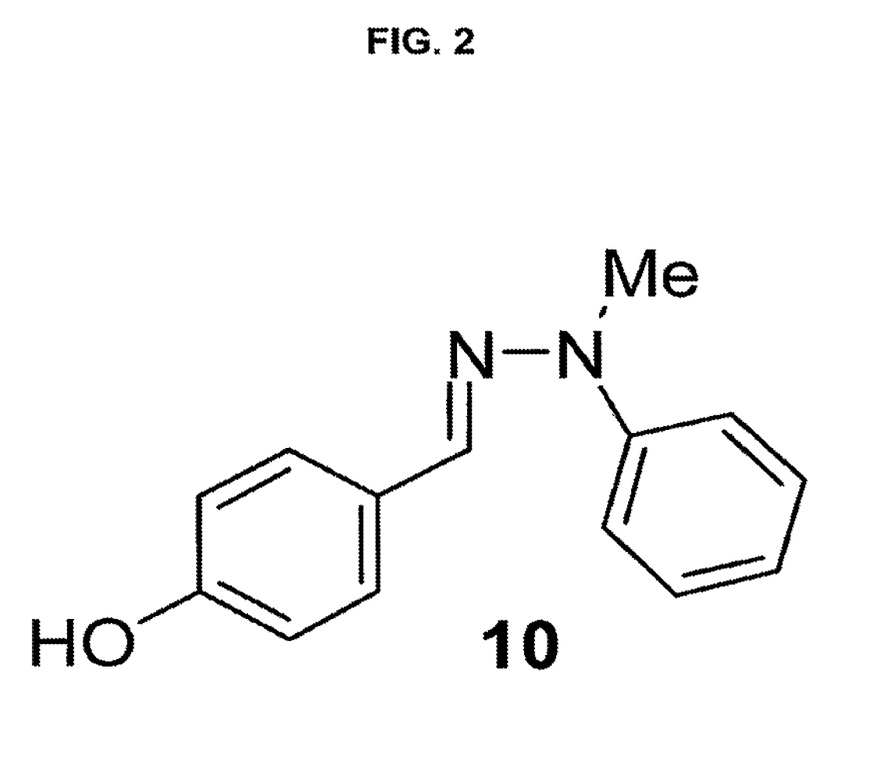
FIG. 2 is a chemical formula for compound 10, a di-substituted hydrazone.

To determine if the activity would be affected by disubstitution on the nitrogen, compound 10 was synthesized (FIG. 2). Methylation of phenyl hydrazine (5) with methyl iodide and sodium amide afforded N-methyl-N-phenyl hydrazine. Hydrazone formation under typical conditions gave 10 in 86% yield. Compound 10 was a very weak inhibitor of MIF activity, displaying an $IC_{50}$ value of 300 µM. This observation could be accounted for by increased steric hinderance or by the reduced number of hydrogen bonding interactions between the di-substituted hydrazone derivative 10 and the active site of MIF.

To further investigate the structure-activity relationship between the hydrazones and MIF another class of compounds, the phenolic hydrazone carbamates, were evaluated. The phenolic hydrazone carbamates 11-15 and 18 were chosen as they displayed key functionalities similar to those of the amino acid Schiff base 1 and 2 (Table 2). These functionalities are the hydroxyl group, phenyl ring and the carboxylate moiety. It has been reported that a secondary hydrogen bond interaction exists between the carboxylate moiety of 2 and lysine-32A of the MIF active site (Dios et al., 2002). Improvement in the inhibition of MIF tautomerase activity of approximately 10-fold was observed on changing the methyl group of 11 ($IC_{50}$=55 µM) to the more lipophilic t-butyl moiety 13 ($IC_{50}$=5.5 µM). To determine if phenyl rings improve the inhibition of MIF activity, the t-butyl carbamate was replaced with a benzyl carbamate 14 and p-methoxy benzyl carbamate 15. This change from a bulky alkyl 13 to an aromatic group 14-15 ($IC_{50}$=10, 8 µM) resulted in a slight decrease in the inhibitory effect.

Biological Activity.

Figure 3:
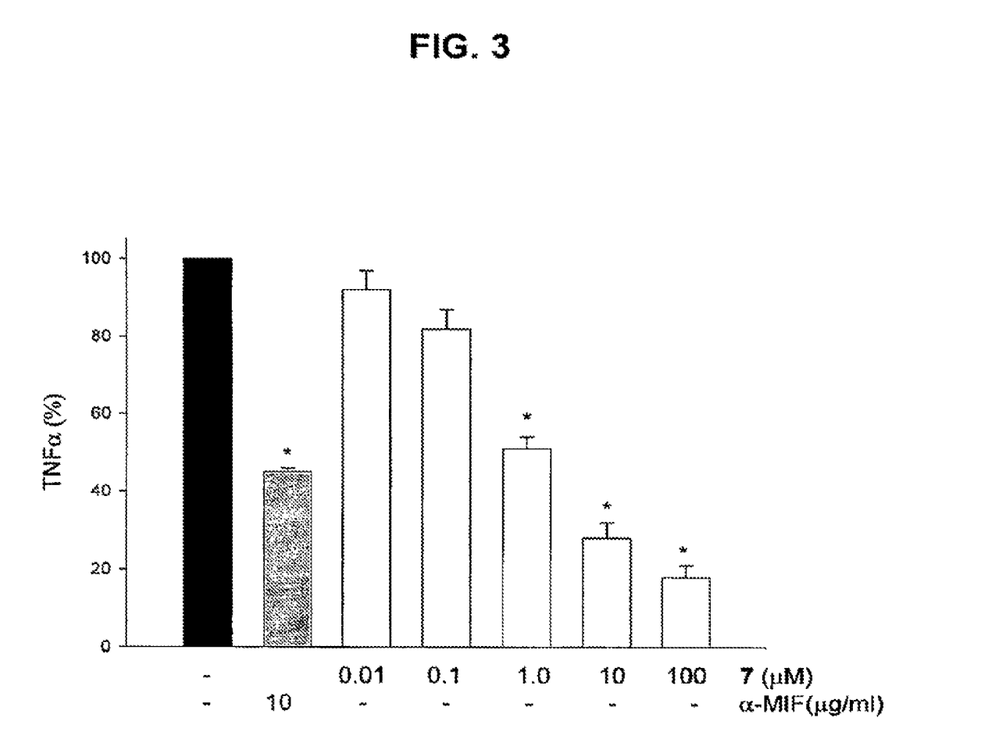
FIG. 3 is a graph of experimental results showing that compound 7 inhibits TNF secretion from LPS-treated macrophages. RAW 267.4 macrophages (10$^5$) were treated with various concentrations of compound 7 (0.01-100 µM) 30 min prior to LPS addition or 10 µg/ml of mouse monoclonal antibody against MIF (XIV.15.5; α-MIF). After 16 h of incubation, cell culture supernatants were collected for determination of TNFα concentration by ELISA. Data are presented as mean±S.D. (n=3, *, p<0.01)

Intracellular MIF occupies a critical role in mediating the cellular responses to pathways activated by lipopolysaccharide (LPS) endotoxin (Roger et al., 2001) and MIF-deficient cells are hyporesponsive to endotoxin (Bozza et al., 1999). MIF null macrophages can produce 50-60% less TNF compared to wild type (Al-Abed et al., 2005; Mitchell et al., 2002). Additionally, anti-MIF antibody (10 µg/ml) inhibits 50% of TNF release from LPS-treated macrophages (Al-Abed et al., 2005). Compound 2 (ISO-1) dose-dependently inhibits LPS-induced TNF release from wild-type but not MIF null macrophages, suggesting that the chemical inhibitor of MIF is specific. Accordingly, it was reasoned that compound 7 binding to MIF would suppress LPS responses in macrophages. Compound 7 dose-dependently did inhibit LPS-induced TNF release (FIG. 3). Thus, compound 7 recapitulates the phenotype of the MIF deficient macrophages and is associated with decreased TNF production in response to LPS.

Figure 4:
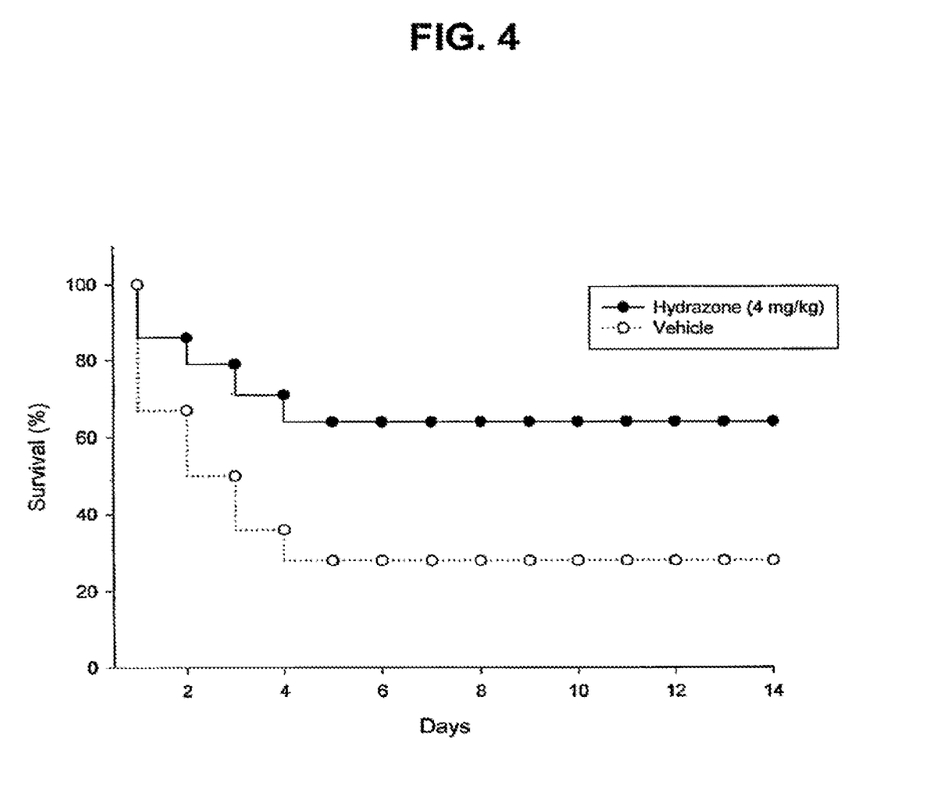
FIG. 4 is a graph of experimental results showing that the hydrazone compound 7 is protective after 24 h late treatment in a CLP model. Mice were injected intraperitoneally with compound 7 ("hydrazone") (4 mg/kg) (n=13, p<0.01) or vehicle 24 h after CLP (n=13). A single injection was composed of 100 µg of Compound 7 (equivalent to 4 mg/kg) in 200 µL of 20% DMSO: 80% saline solution. Additional administrations of compound 7 (bi-daily) were given on days 2 and 3.

The importance of MIF as a molecular therapeutic target in sepsis has been confirmed by the recent observation that treatment with anti-MIF antibodies or compound 2 significantly improves survival in septic mice (Al-Abed et al., 2005). Further, serum MIF levels increased to 70% of maximum levels within 24 h post CLP, and peaked at 36 h (Al-Abed et al., 2005). This identified MIF as a late mediator in sepsis and indicated the therapeutic potential of inhibiting MIF in a clinically relevant time frame. Therefore, it was reasoned that a delayed treatment with compound 7, consistent with the kinetics of MIF release, could be successfully applied to improve survival in sepsis. The ability of compound 7 to improve the survival rate in cecal ligation and puncture (CLP)-induced peritonitis, a widely used preclinical model of sepsis, was tested. Intraperitoneal treatment of 7 (4 mg/kg) initiated 24 h after CLP surgery and continued for 3 days resulted in a survival rate of 65% (p<0.01) compared to 28% in the control (vehicle-treated) group (FIG. 4). Thus, compound 7 treatment provides significant protection against sepsis lethality, comparable to the effect of anti-MIF antibody and compound 2 (Al-Abed et al., 2005). Remarkably, a dose of compound 7, 10-fold less than 2, achieved similar protection. This finding indicates an association between the potency of compound 7 in inhibiting the MIF tautomerase active site and its beneficial effect of improving survival in experimental sepsis.

In summary, phenolic hydrazones were designed and synthesized as non toxic, potent MIF antagonists. The structure-activity relationship study suggests that minor changes in functionalization of the hydrazones affect the binding of these compounds to the MIF tautomerase active site. Notably, compound 7 exhibits the greatest activity of all the compounds tested and is so far the most potent inhibitor of MIF described in the literature (Al-Abed et al., 2005; Dios et al., 2002; Cheng and Al-Abed, 2006; Orita et al, 2001; Orita et al., 2002).

Compound 7 exhibited a potent anti-inflammatory activity in vitro as demonstrated by suppression of LPS-induced macrophage activation (FIG. 3). Moreover, a relatively low concentration of this small molecule MIF inhibitor improved survival in sepsis when treatment was initiated at 24 hours after the onset of the disease.

Sepsis is a complex inflammatory disorder and its clinical management is a challenging health issue. Therefore, the finding that compound 7 is effective at 24 hours after the onset of the disorder could be of considerable clinical interest. Additionally, anti-cytokine agents that show efficacy in rodent sepsis models have proved to be valuable therapeutics for a variety of human inflammatory and autoimmune diseases and conditions, such as rheumatoid arthritis and Crohn's disease.

Experimental Section

General Experimental.

All chemicals were obtained from commercial suppliers and used without further purification. Aluminium-backed Silica Gel 60 with a 254 nm fluorescent indicator TLC plates were used. Developed TLC plates were visualized under a short-wave UV lamp, stained with an $I_2$—$SiO_2$ mixture. Flash column chromatography (FCC) was performed using flash silica gel (32-63 µm) and usually employed a stepwise solvent polarity gradient, correlated with TLC mobility. Melting points (M.p.) were determined in a Gallenkamp Melting Point Apparatus in open capillaries and are uncorrected. IR spectra were obtained on a Thermo Nicolet IR 100 FT-IR spectrometer. All $^1H$ spectra were recorded either on a Jeol spectrometer or a GE QE 300 spectrometer at 270 or 300 MHz. The $^{13}C$ spectra were recorded on a GE QE 300 spectrometer at 75 MHz. Chemical shifts are relative to the deuterated solvent peak and are in parts per million (ppm). The coupling constants (J) are measured in Hertz (Hz). The $^1H$ signals are described as s (singlet), d (doublet), t (triplet), q (quartet), m (multipet) and br s (broad singlet). Low and high resolution mass spectroscopy was carried out at the Mass Spectrometry Facility at the University of Illinois at Urbana-Champaign.

General Experimental for compounds 3-5 and 10-19.

4-Hydroxybenzaldehyde (122 mg, 1 mmol) or 3-fluoro-4-hydroxybenzaldehyde (140 mg, 1 mmol) and the hydrazide (2 mmol) were dissolved in ethanol (10 mL). To this was added acetic acid (1 mmol) and the reaction was stirred overnight at room temperature. Removal of the ethanol in vacuo afforded an oily residue. The residue was taken up with ethyl acetate and washed with water. The organic layer was separated and dried with anhydrous $Na_2SO_4$. Concentration in vacuo afforded a residue which was subsequently purified by FCC using hexane and ethyl acetate as eluent (4:1) to give compounds 3-5 and 10-15.

General Procedure for Compounds 6-9.

4-Hydroxybenzaldehyde (122 mg, 1 mmol) or 3-fluoro-4-hydroxybenzaldehyde (140 mg, 1 mmol) or 3-chloro-4-hydroxybenzaldehyde (156 mg, 1 mmol) or 3-bromo-4-hydroxybenzaldehyde (201 mg, 1 mmol) and 4-methoxyphenylhydrazine hydrochloride (350 mg, 2 mmol) were suspended in methanol (10 mL). To this suspension was added a 2M aqueous solution of sodium hydroxide (60 mg, 1.5 mmol) and the reaction was stirred overnight at room temperature. Upon completion of the reaction, the solution was then acidified to pH 4 by the addition of 1M HCl. Removal of the methanol in vacuo afforded an oily residue. The residue was taken up with ethyl acetate and washed with water. The organic layer was separated and dried with anhydrous $Na_2SO_4$. Concentration in vacuo afforded a residue which was subsequently purified by FCC using hexane and ethyl acetate as eluent (4:1) to give compounds 6-9.

Spectrophotometric Assay for Enzymatic Activity.

A fresh stock solution of L-dopachrome methyl ester (2.4 nM) was generated by oxidation of L-3,4-dihydroxyphenylalanine methyl ester with sodium periodate, producing an orange-colored solution. Activity was determined at room temperature by adding dopachrome methyl ester (0.3 mL) to a cuvette containing 1 µL of MIF solution (850 ng/mL) in 50 mM potassium phosphate buffer, pH 6, and measuring the decrease in absorbance from 2 to 20 s at 475 nm spectrophotometrically. The inhibitors 3-15 were dissolved in DMSO at various concentrations (0.1-100 µM) and 1 µL was added to the cuvette with the MIF prior to the addition of the dopachrome.

Cellular Assay.

Compound 7 inhibits TNF secretion from LPS-treated macrophages. RAW 267.4 macrophages ($10^5$) were treated with various concentrations of hydrazone 7 (0.01-100 µM) 30 min prior to LPS addition. After 16 h of incubation, cell culture supernatants were collected for determination of TNF concentration by ELISA. Data are presented as mean±S.D. (n=3, *, p<0.01).

Animal studies.

All animal experiments were approved by the Institutional Animal Care and Use Committee of the North Shore-Long Island Jewish Research Institute. Male Balb/C mice, ~8 weeks old, were subjected to cecal ligation and puncture. Details of the CLP procedure has been carried out as follows: In anesthetized male Balb/C mice (ketamine 100 mg/kg and xylazine 8 mg/kg administered intramuscularly) the cecum was ligated and given a single puncture. Abdominal access was gained via a midline incision. The cecum was isolated and ligated with a 6-0 silk ligature below the ileocecal valve, and the cecum punctured once with a 22 G needle, stool (approximately 1 mm) extruded from the hole, and the cecum placed back into the abdominal cavity. The abdomen was closed with two layers of 6-0 Ethilon sutures. Antibiotics were administered immediately after CLP (Premaxin 0.5 mg/kg, subcutaneously, in a total volume of 0.5 ml/mouse) and single dose of resuscitative fluid (normal saline solution administered subcutaneously (20 ml/kg-body weight) immediately after CLP surgery (Wang et al, 1999). Mice were injected intraperitoneally with 4 mg/kg (n=13, **P<0.01) or vehicle 24 hours after CLP (n=13). Additional two injections were given on day 2 and 3. Vehicle (aqueous 20% DMSO) or compound 7 (4 mg/kg; intraperitoneally) treatment was started 24 h after the induction of sepsis and repeated twice daily on days 2 and 3. Animal survival was monitored for 14 days.

NMR Data

Compound 3: Yellow solid (90%). M.p. 248-250° C. IR (nujol mull) ν cm$^{-1}$: 3220, 3315, 1650, 1603, 1568, 1506. $^1$H NMR (300 MHz, CD$_3$OD) δ 6.99 (d, 2H, J=8.8 Hz, H3, H5), 7.94 (d, 2H, J=8.8 Hz, H2, H6), 8.87 (s, 1H, H7). $^{13}$C NMR (75 MHz, CD$_3$OD) δ 117.9 (C3, C5), 121.7 (C1), 134.7 (C4, C6), 163.2 (C7), 166.1 (C4). MS (ESI) 137.1 (M+1, 25). ESIHRMS m/z calcd for C$_7$H$_9$N$_2$O 137.0715, found 137.0719.

Compound 4: Red solid (85%). M.p. 58-60° C. IR (nujol mull) ν cm$^{-1}$: 3361, 1671, 1604, 1513. $^1$H NMR (300 MHz, (CD$_3$)$_2$CO) δ 2.81 (d, 3H, J=33 Hz, Me), 6.87 (d, 2H, J=8.8 Hz, H3, H5), 7.42 (d, 2H, J=8.8 Hz, H2, H6), 7.95 (s, 1H, H7), 8.35 (br s, 2H, OH, NH, D$_2$O exchangeable). $^{13}$C NMR (75 MHz, (CD$_3$)$_2$CO) δ 36.1 (Me), 116.5 (C3, C5), 127.9 (C1), 129.6 (C2, C6), 151.2 (C7), 157.8 (C4). MS (ESI) 151.1 (M+1, 100), 152.1 (M+2, 8). ESIHRMS m/z calcd for C$_8$H$_{11}$N$_2$O 151.0871, found 151.0874.

Compound 5: Brown solid (88%). M.p. 154-156° C. IR (nujol mull) ν cm$^{-1}$: 3406, 3291, 1599, 1508. $^1$H NMR (300 MHz, (CD$_3$)$_2$CO) δ 6.70 (dd, 1H, J=7.5, 1.2 Hz, H4'), 6.82 (d, 2H, J=8.4 Hz, H3, H5), 7.07 (dd, 1H, J=7.5, 1.2 Hz, H2', H6'), 7.16 (t, 2H, J=7.5 Hz, H3', H5'), 7.50 (d, 2H, J=8.4 Hz, H2, H6), 7.77 (s, 1H, H7), 8.50 (br s, 1H, D$_2$O exchangeable), 9.15 (s, 1H, D$_2$O exchangeable). $^{13}$C NMR (75 MHz, (CD$_3$)$_2$CO) δ 113.1 (C2', C6'), 116.4 (C3, C5), 119.5 (C4'), 128.2 (C3', C5'), 128.8 (C1), 129.8 (C2, C6), 138.2 (C7), 146.9 (C1'), 158.6 (C4). MS (ESI) 213.1 (M+1, 85), 214.1 (M+2, 10). ESIHRMS m/z calcd for C$_{13}$H$_{13}$N$_2$O 213.1028, found 213.1030.

Compound 6: Brown residue (84%). IR (nujol mull) ν cm$^{-1}$: 3419, 1681, 1670, 1650, 1635, 1603, 1507. $^1$H NMR (300 MHz, (CD$_3$)$_2$CO) δ 3.65 (s, 3H, OMe), 6.78 (d, 2H, J=8.7 Hz, H3', H5'), 6.80 (d, 2H, J=8.4 Hz, H3, H5), 7.01 (d, 2H, J=8.7 Hz, H2', H6'), 7.47 (d, 2H, J=8.4 Hz, H2, H6), 7.72 (s, 1H, H7), 8.40 (br s, 1H, D$_2$O exchangeable), 8.91 (s, 1H, D$_2$O exchangeable). $^{13}$C NMR (75 MHz, (CD$_3$)$_2$CO) δ 55.9 (OMe), 114.7 (C3', C5'), 115.4 (C2', C6'), 116.6 (C3, C5), 128.4 (C1), 130.2 (C2, C6), 137.2 (C7), 141.2 (C1'), 151.2 (C4'), 163.9 (C4). MS (ESI) 241.1 (M−1, 65). ESIHRMS m/z calcd for C$_{14}$H$_{13}$N$_2$O$_2$ 241.0977, found 241.0981.

Compound 7: Brown solid (89%). M.p. 120-121° C. IR (nujol mull) ν cm$^{-1}$: 3319, 3302, 1619, 1514. $^1$H NMR (300 MHz, (CD$_3$)$_2$CO) δ 3.69 (s, 3H, OMe), 6.80 (d, 2H, J=8.8 Hz, H3', H5'), 6.95 (t, 1H, J=8.8 Hz, H5), 7.04 (d, 2H, J=8.8 Hz, H2', H6'), 7.21 (d, 1H, J=8.4 Hz, H6), 7.42 (dd, 1H, J=10.6, 1.8 Hz, H2), 7.70 (s, 1H, H7), 8.78 (br s, 1H, D$_2$O exchangeable), 9.11 (s, 1H, D$_2$O exchangeable). $^{13}$C NMR (75 MHz, (CD$_3$)$_2$CO) δ 56.0 (OMe), 113.3 (J$_{CCF}$=19.5 Hz, C2), 114.3 (C3', C5'), 115.5 (C2', C6'), 118.7 (C5), 123.4 (C6), 130.2 (J$_{CCF}$=4.9 Hz, C1), 135.9 (C7), 140.7 (C1'), 145.6 (J$_{CCF}$=13.7 Hz, C4), 152.6 (J$_{CF}$=239.2 Hz, C3), 154.4 (C4'). MS (ESI) 261.1 (M+1, 30), 262.1 (M+2, 6). ESIHRMS m/z calcd for C$_{14}$H$_{14}$N$_2$O$_2$F 261.1039, found 261.1048.

Compound 8: Brown solid (89%). M.p. 108-110° C. IR (nujol mull) ν cm$^{-1}$: 1601, 1557, 1501. $^1$H NMR (300 MHz, (CD$_3$)$_2$CO) δ 3.69 (s, 3H, OMe), 6.80 (d, 2H, J=8.8 Hz, H3', H5'), 7.03 (d, 2H, J=8.8 Hz, H2', H6'), 7.13 (d, 1H, J=8.4 Hz, H5), 7.32 (dd, 1H, J=6.6, 1.8 Hz, H6), 7.54 (d, 1H, J=1.8 Hz, H2), 7.67 (s, 1H, H7), 8.80 (br s, 1H, D$_2$O exchangeable), 9.12 (s, 1H, D$_2$O exchangeable). $^{13}$C NMR (75 MHz, (CD$_3$)$_2$CO) δ 55.9 (OMe), 114.3 (C3', C5'), 115.5 (C2', C6'), 117.8 (C5), 121.6 (C3), 126.4 (C6), 127.6 (C2), 130.6 (C1), 135.5 (C7), 140.6 (C1'), 153.5 (C4), 154.4 (C4'). MS (ESI) 277.1 (MCl$^{35}$+1, 60), 279.1 (MCl$^{37}$+1, 25). ESIHRMS m/z calcd for C$_4$H$_{13}$N$_2$O$_2$Cl 277.0744, found 277.0739.

Compound 9: Brown solid (90%). M.p. 135-137° C. IR (nujol mull) ν cm$^{-1}$: 3453, 3305, 1597. $^1$H NMR (300 MHz, (CD$_3$)$_2$CO) δ 3.69 (s, 3H, OMe), 6.80 (d, 2H, J=8.8 Hz, H3', H5'), 6.97 (d, 1H, J=8.4 Hz, H5), 7.03 (d, 2H, J=8.8 Hz, H2', H6'), 7.45 (dd, 1H, J=6.2, 2.2 Hz, H6), 7.69 (s, 1H, H7), 7.78 (d, 1H, J=1.8 Hz, H2), 8.85 (s, 1H, D$_2$O exchangeable), 9.15 (s, 1H, D$_2$O exchangeable). $^{13}$C NMR (75 MHz, (CD$_3$)$_2$CO) δ 55.9 (OMe), 110.8 (C3), 114.2 (C3', C5'), 115.5 (C2', C6'), 117.4 (C5), 127.1 (C6), 130.8 (C2), 131.0 (C1), 135.3 (C7), 140.6 (C1'), 154.4 (C4'), 154.5 (C4). MS (ESI) 321.0 (MBr$^{79}$+1, 100), 323.0 (MBr$^{81}$+1, 80). ESIHRMS m/z calcd for C$_{14}$H$_{13}$N$_2$O$_2$Br 321.0239, found 321.0240.

Compound 10: White solid (86%). M.p. 93-95° C. IR (nujol mull) ν cm$^{-1}$: 3300, 1600, 1506. $^1$H NMR (300 MHz, (CD$_3$)$_2$CO) δ 3.38 (s, 3H, Me), 6.81 (t, 1H, J=8.4 Hz, H4'), 6.83 (d, 2H, J=8.8 Hz, H3, H5), 7.24 (t, 2H, J=8.4 Hz, H3', H5'), 7.37 (dd, 2H, J=8.1, 1.1 Hz, H2', H6'), 7.57 (d, 2H, J=8.8 Hz, H2, H6), 7.60 (s, 1H, H7), 8.43 (s, 1H, OH, D$_2$O exchangeable). $^{13}$C NMR (75 MHz, (CD$_3$)$_2$CO) δ 33.1 (Me), 115.2 (C2', C6'), 116.3 (C3, C5), 120.5 (C4'), 128.3 (C3', C5'), 129.6 (C2, C6), 129.8 (C1), 133.5 (C7), 149.2 (C1'), 158.3 (C4). MS (ESI) 227.1 (M+1, 100), 228.1 (M+2, 20). ESIHRMS m/z calcd for C$_{14}$H$_{15}$N$_2$O 227.1184, found 227.1174.

Compound 11: White solid (90%). M.p. 165-167° C. IR (nujol mull) ν cm$^{-1}$: 3253, 1651, 1635, 1606, 1556, 1514. $^1$H NMR (300 MHz, (CD$_3$)$_2$CO) δ 3.78 (s, 3H, OMe), 6.93 (d, 2H, J=8.8 Hz, H3, H5), 7.60 (d, 2H, J=8.8 Hz, H2, H6), 8.08 (s, 1H, H7), 8.78 (s, 1H, D$_2$O exchangeable), 9.85 (br s, 1H, D$_2$O exchangeable). $^{13}$C NMR (75 MHz, (CD$_3$)$_2$CO) δ 52.4 (OMe), 116.4 (C3, C5), 127.4 (C1), 129.3 (C2, C6), 144.9 (C7), 154.9 (C4), 159.8 (C=O). MS (ESI) 195.1 (M+1, 100), 196.1 (M+2, 10). ESIHRMS m/z calcd for C$_9$H$_{11}$N$_2$O$_3$ 195.0770, found 195.0776.

Compound 12: White solid (89%). M.p. 189-190° C. IR (nujol mull) ν cm$^{-1}$: 3338, 3202, 1678, 1607, 1581, 1558, 1513. $^1$H NMR (300 MHz, (CD$_3$)$_2$CO) δ 1.21 (t, 3H, J=7.0 Hz, OCH$_2$CH$_3$), 4.13 (q, 2H, J=7.0 Hz, OCH$_2$CH$_3$), 6.84 (d, 2H, J=8.8 Hz, H3, H5), 7.50 (d, 2H, J=8.8 Hz, H2, H6), 8.00 (s, 1H, H7), 8.73 (br s, 1H, D$_2$O exchangeable), 9.74 (br s, 1H, D$_2$O exchangeable). $^{13}$C NMR (75 MHz, (CD$_3$)$_2$CO) δ 15.1 (OCH$_2$CH$_3$), 61.5 (OCH$_2$CH$_3$), 116.4 (C3, C5), 127.5 (C1), 129.3 (C2, C6), 144.8 (C7), 154.4 (C4), 159.8 (C=O). MS (ESI) 209.1 (M+1, 100), 210.1 (M+2, 10). ESIHRMS m/z calcd for C$_{10}$H$_{13}$N$_2$O$_3$ 209.0926, found 209.0932.

Compound 13: White solid (89%). M.p. 155-156° C. IR (nujol mull) □ν cm$^{-1}$: 3346, 3243, 1660, 1608, 1578, 1534, 1510. $^1$H NMR (300 MHz, (CD$_3$)$_2$CO) δ 1.48 (s, 9H, C(CH$_3$)$_3$), 6.87 (d, 2H, J=8.8 Hz, H3, H5), 7.53 (d, 21, J=8.8 Hz, H2, H6), 8.01 (s, 1H, H7), 8.69 (br s, 1H, D$_2$O exchangeable), 9.58 (br s, 1H, D$_2$O exchangeable). $^{13}$C NMR (75 MHz, (CD$_3$)$_2$CO) δ 28.7 (C(CH$_3$)$_3$), 80.2 (C(CH$_3$)$_3$), 116.4 (C3, C5), 127.7 (C1), 129.2 (C2, C6), 144.2 (C7), 153.4 (C4), 159.6 (C=O). MS (ESI) 237.1 (M+1, 30), 238.1 (M+2, 5). ESIHRMS m/z calcd for C$_{12}$H$_1$N$_2$O$_3$ 237.1239, found 237.1249.

Compound 14: White solid (90%). M.p. 159-160° C. IR (nujol mull) ν cm$^{-1}$: 3397, 1668, 1606, 1556, 1506. $^1$H NMR (300 MHz, (CD$_3$)$_2$CO) δ 5.16 (s, 2H, OCH$_2$), 6.84 (d, 2H, J=8.4 Hz, H3, H5), 7.26-7.35 (m, 3H, ArCH), 7.36 (d, 2H, J=8.8 Hz, ArCH) 7.51 (d, 2H, J=8.4 Hz, H2, H6), 8.00 (s, 1H, H7), 8.71 (s, 1H, D$_2$O exchangeable), 9.91 (br s, 1H, D$_2$O exchangeable). $^{13}$C NMR (75 MHz, (CD$_3$)$_2$CO) δ 67.1 (OCH$_2$Ar), 116.4 (C3, C5), 127.4 (C1), 128.8 (CH), 129.2 (C2, C6), 129.3 (CH), 137.9 (CCH), 145.2 (C7), 154.3 (C4), 159.8

(C=O). MS (ESI) 271.1 (M+1, 100), 272.1 (M+2, 10). ESI-HRMS m/z calcd for $C_{15}H_{15}N_2O_3$ 271.1083, found 271.1089.

Compound 15: White solid (89%). M.p. 147-148° C. IR (nujol mull) $v\, cm^{-1}$: 3412, 3270, 1683, 1602, 1543, 1514. $^1$H NMR (300 MHz, $(CD_3)_2CO$) δ 3.76 (s, 3H, OMe), 5.08 (s, 2H, $OCH_2$), 6.83 (d, 2H, J=8.4 Hz, H3, H5), 6.89 (d, 2H, J=8.8 Hz, CHCOMe), 7.33 (d, 2H, J=8.4 Hz, CHCCOMe), 7.51 (d, 2H, J=8.8 Hz, H2, H6), 8.00 (s, 1H, H7), 8.70 (s, 1H, $D_2O$ exchangeable), 9.82 (br s, 1H, $D_2O$ exchangeable). $^{13}$C NMR (75 MHz, $(CD_3)_2CO$) δ 55.6 (OMe), 66.9 ($OCH_2$), 114.6 (C3, C5), 116.4 (CCOMe), 127.4 (C1), 129.3 (C2, C6), 129.8 (CCCCOMe), 1$\overline{3}$0.7 (CCCCOMe), 145.0 (C7), 154.3 (C4), 1$\overline{5}$9.8 (C=O), 160.6 ($\overline{C}$OMe). MS (ESI) 301.1 (M+1, 25), 302.1 (M+2, 5). ESIH$\overline{R}$MS m/z calcd for $C_{16}H_7N_2O_4$ 301.1188, found 301.1200.

Compound 16: white solid (86%). $^1$H NMR (300 MHz, $(CD_3)_2CO$) v 3.76 (s, 3H), 5.08 (s, 2H), 6.82 (d, J=8.4 Hz, 2H), 6.87 (d, J=8.8 Hz, 2H), 7.31 (d, J=8.4 Hz, 2H), 7.49 (d, J=8.8 Hz, 2H), 7.99 (s, 1H), 8.70 (s, 1H). MS: m/z 299.5 (M-H).

Compound 17: white solid (87%). $^1$H NMR (270 MHz, $(CD_3)_2CO$) δ 6.89 (d, J=7.9 Hz, 2H), 7.54 (m, 5H), 7.94 (d, J=7.9 Hz, 2H), 8.40 (s, 1H), 8.85 (s, 1H). MS: m/z 239.3 (M-H).

Compound 18: white solid (89%). $^1$H NMR (300 MHz, $(CD_3)_2CO$) δ 1.44 (s, 9H), 6.98 (dd, J=2.5, 8.4, 1H), 7.27 (d, J=8.0 Hz, 1H), 7.41 (dd, J=2.2, 12.1 Hz, 1H), 7.97 (s, 1H), 8.98 (s, 1H). MS: m/z 253.3 (M-H).

Compound 19: brown solid (87%). $^1$H NMR (270 MHz, $(CD_3)_2CO$) δ 6.77 (t, J=6.9 Hz, 1H), 7.01 (t, J=8.4 Hz, 1H), 7.12-7.29 (m, 4H), 7.48 (dd, J=1.7, 10.4 Hz, 1H), 7.77 (s, 1H). MS: m/z 229.7 (M-H).

Spectrophotometric Assay for Enzymatic Activity.

A fresh stock solution of L-dopachrome methyl ester (2.4 nM) was generated by oxidation of L-3,4-dihydroxyphenylalanine methyl ester with sodium periodate, producing an orange-colored solution. Activity was determined at room temperature by adding dopachrome methyl ester (0.3 mL) to a cuvette containing 1 μL of MIF solution (850 ng/mL) in 50 mM potassium phosphate buffer, pH 6, and measuring the decrease in absorbance from 2 to 20 s at 475 nm spectrophotometrically. The inhibitors were dissolved in DMSO at various concentrations (0.1-100 mM) and added to the cuvette with the MIF prior to the addition of the dopachrome.

Animal Studies.

Compound 7 is protective even when treatment is initiated after 24 h in a CLP model (FIG. 4). Mice were injected intraperitoneally with 3.5 mg/kg (n=13, **P<0.01) or vehicle 24 hours after CLP (n=13). Two additional injections were given on day 2 and 3. Details of the CLP procedure has been carried out as follows: In anesthetized male Balb/C mice (ketamine 100 mg/kg and xylazine 8 mg/kg administered intramuscularly). Abdominal access was gained via a midline incision. The cecum was isolated and ligated with a 6-0 silk ligature below the ileocecal valve, and the cecum punctured once with a 22 G needle, stool (approximately 1 mm) extruded from the hole, and the cecum replaced in the abdominal cavity. The abdomen was closed with two layers of 6-0 Ethilon sutures. Antibiotics were administered immediately after CLP (Premaxin 0.5 mg/kg, subcutaneously, in a total volume of 0.5 ml/mouse) and single dose of resuscitative fluid (normal saline solution administered subcutaneously (20 ml/kg-body weight) immediately after CLP surgery (Wang et al., 1999).

Example 2

Effect of Compound 7 on Leukocyte Recruitment in Response to Acute Inflammation

Air pouches were made according to standard procedures (Garcia-Ramallo et al., 2002) on Swiss Webster male mice (25-30 g) by injecting sterile air s.c. on day 0 (6 ml) and day 3 (3 ml). On day 6, animals were treated with vehicle (350 μl of 20% DMSO) or compound 7 (7 mg/kg) either intraperitoneal (i.p.) or gavage (oral) as indicated. After 15 min, the animals were challenged by injecting 1 ml 1% carrageenan (in PBS) into the air pouch cavity. Five hrs after carrageenan injection the animals were sacrificed, the pouches washed with PBS, exudate collected, and the total number of infiltrating cells quantitated. The plot shows the number of cells normalized to that seen with vehicle alone (veh.).

Figure 5:
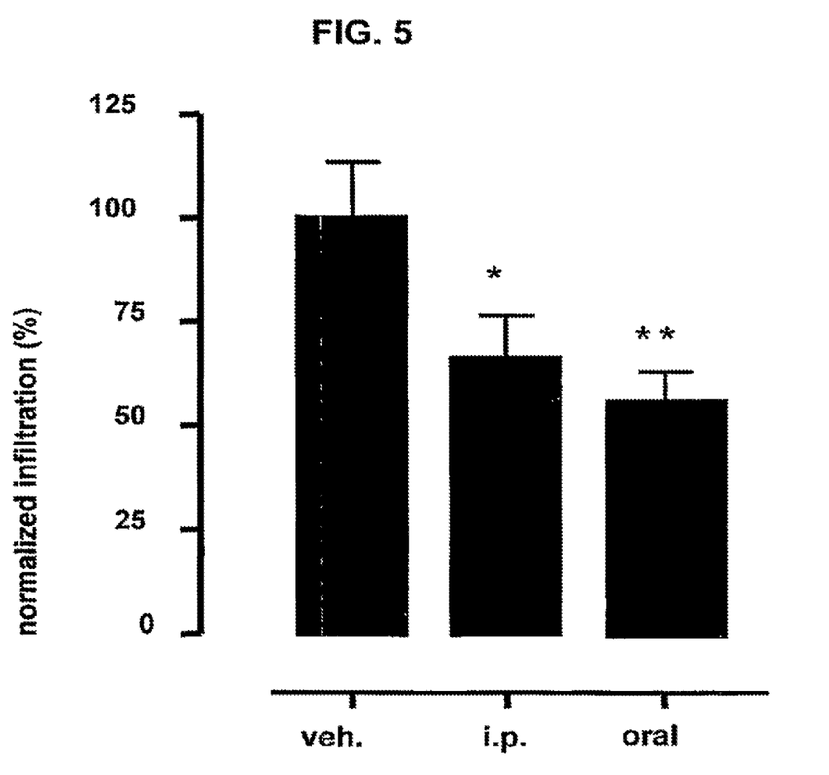
FIG. 5 is a graph of experimental results showing that compound 7, administered either orally or I.P., inhibits leukocyte recruitment in an established model of acute inflammation. *$p<0.05$ (n=5); **$p<0.006$ (n=20) relative to vehicle alone.

Results are shown in FIG. 5. Both the i.p. and oral treatments with compound 7 showed a significant reduction in leukocyte recruitment in response to the inflammation caused by the carrageenan treatment into the air pouch cavity.

In another experiment, air pouches were made as above. On day 6, animals were treated with vehicle (350 μl of 20% DMSO) or compound 7 (7 mg/kg, gavage) at the indicated times prior to sacrificing and cell harvesting. In all cases, 1% carrageenan was injected into the air pouch cavity 5 hrs before sacrificing.

Figure 6:
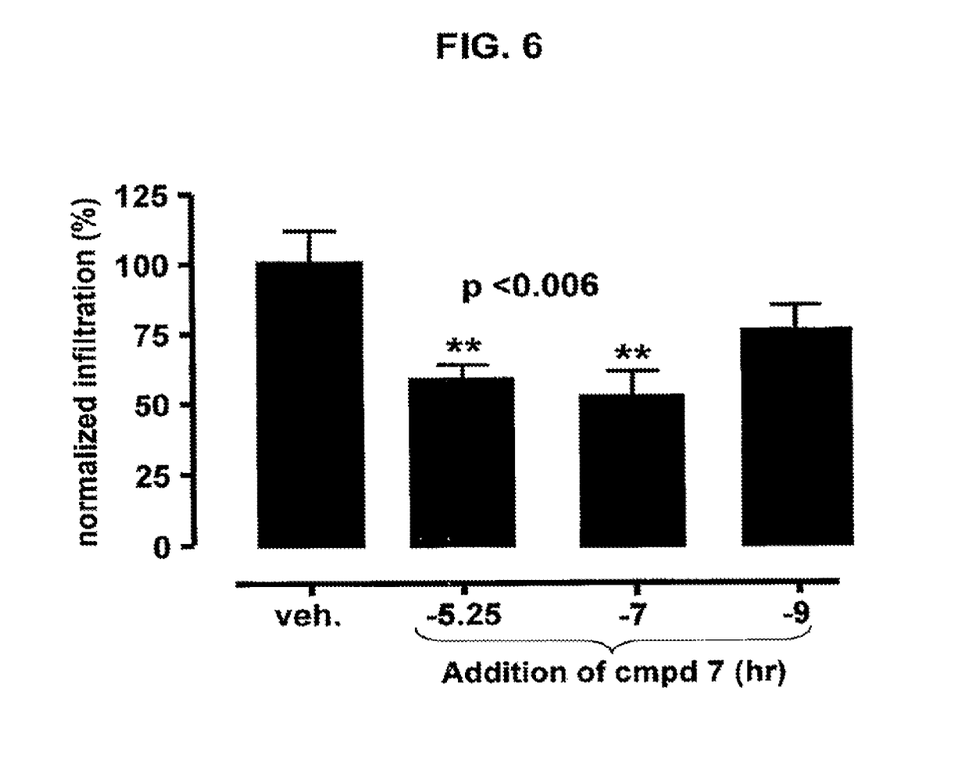
FIG. 6 is a graph of experimental results showing that compound 7 has an apparent biological half-life of 7-9 hrs as assessed by inhibition of leukocyte infiltration in an air pouch model challenged with carrageenan. **$p<0.006$ (n=20) relative to vehicle alone.

Results are shown in FIG. 6. The plot shows the number of cells normalized to that seen with vehicle alone (veh.). When the mice were treated orally with compound 7 at 5.25 and 7 hours, but not 9 hours, before harvesting air pouch cells for quantitation, a significant reduction in leukocyte recruitment was observed. This indicates that with oral administration, compound 7 has an apparent biological half-life of 7-9 hours.

Example 3

Compound 7 Protects Mice from Fatal Endotoxemia

Endotoxemia was induced in Balb/C mice by injection of LPS (16 mg/kg, top or 19 mg/kg, bottom). Mice were treated with either vehicle (350 μl 20% DMSO) or compound 7 (7 mg/kg) i.p., 2 hrs before and 24 after LPS infusion. Survival of the mice was monitored.

Figure 7:
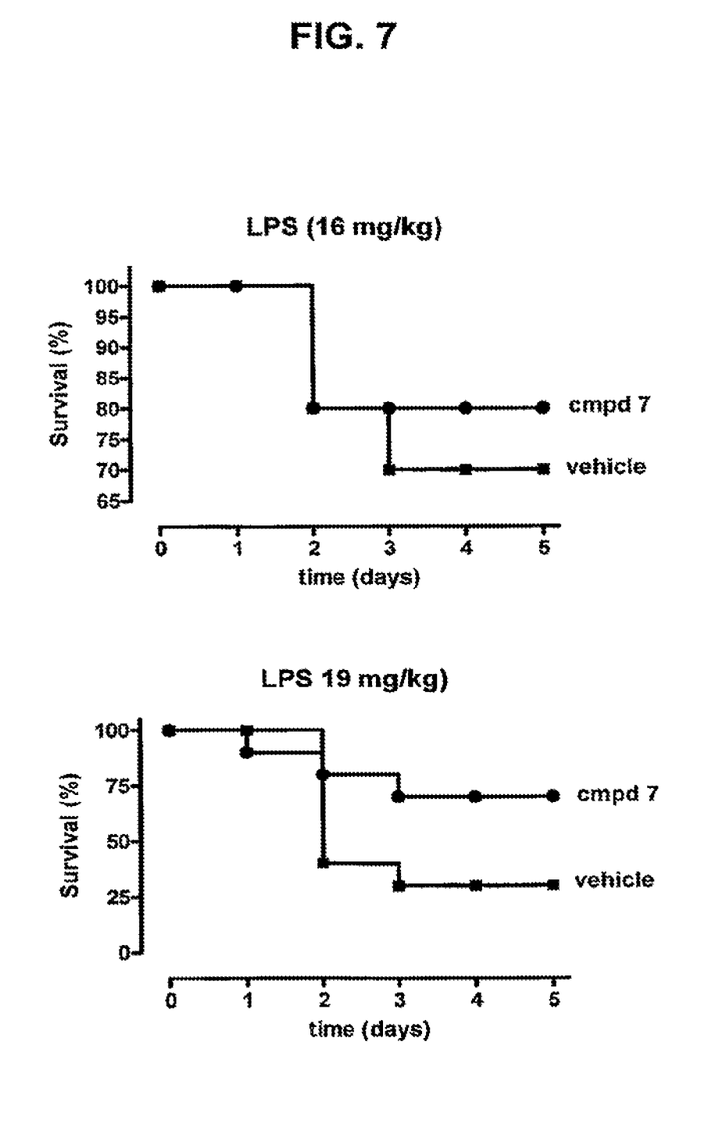
FIG. 7 is a graph of experimental results showing that compound 7 is a protective agent in an animal model of endotoxemia.

Results are shown in FIG. 7. Compound 7 afforded protection to the mice from otherwise fatal LPS exposure.

REFERENCES

Al-Abed, Y.; Dabideen, D.; Aljabari, B.; Valster, A.; Messmer, D. et al. ISO-1 binding to the tautomerase active site of MIF inhibits its pro-inflammatory activity and increases survival in severe sepsis. *J. Biol. Chem.* 2005, 280, 36541-35644.

Bozza, M.; Satoskar, A. R.; Lin, G.; Lu, B.; Humbles, A. A. et al. Targeted disruption of migration inhibitory factor gene reveals its critical role in sepsis. *J. Exp. Med.* 1999, 189, 341-346.

Calandra, T.; Echtenacher, B.; Roy, D. L.; Pugin, J.; Metz; C. N.; Hultner, L.; Heumann, D.; Mannel, D.; Bucala, R.; Glauser, M. P. Protection from septic shock by neutralization of macrophage migration inhibitory factor. *Nat. Med.* 2000, 6, 164-170.

Calandra, T.; Roger, T. Macrophage migration inhibitory factor: a regulator of innate immunity. *Nat. Rev. Immunol.* 2003, 3, 791-800.

Cvetkovic, I.; Al-Abed, Y. et al. Critical role of macrophage migration inhibitory factor activity in experimental autoimmune diabetes. *Endocrinol.* 2005, 146, 2942-2951.

Cheng, K. F.; Al-Abed, Y. Critical modifications of the ISO-1 scaffold improve its potent inhibition of macrophage migration inhibitory factor (MIF) tautomerase activity. *Bioorg. Med. Chem. Let.* 2006, 16, 3376-9.

Dios, A.; Mitchell, R. A.; Aljabari, B.; Lubetsky, J.; O'Connor, K. A.; Liao, H.; Senter, P. D.; Manogue, K. R.; Lolis, E.; Metz, C.; Bucala, R.; Callaway, D. J. E.; Al-Abed, Y. Inhibition of MIF bioactivity by rational design of pharmacological inhibitors of MIF tautomerase activity. *J. Med. Chem.* 2002, 45, 2410-2416.

Garcia-Ramallo E.; Marques, T. et al. Resident cell chemokine expression serves as the major mechanism for leukocyte recruitment during local inflammation. *J. Immunol.* 2002, 169, 6467-6473

Lubetsky, J. B.; Dios, A.; Han, J.; Aljabari, B.; Ruzsicska, B.; Mitchell, R.; Lolis, E.; Al-Abed, Y. The tautomerase active site of macrophage migration inhibitory factor is a potential target for discovery of novel anti-inflammatory agents. *J. Biol. Chem.* 2002, 277, 24976-24982.

Mitchell, R. A.; Liao, H.; Chesney, J.; Fingerle-Rowson, G.; Baugh, J. et al. Macrophage migration inhibitory factor (MIF) sustains macrophage proinflammatory function by inhibiting p53: regulatory role in the innate immune response. *Proc Natl Acad Sci USA* 2002, 99, 345-350

Orita, M.; Yamamoto, S.; Katayama, N.; Aoki, M.; Takayama, K.; Yamagiwa, Y.; Seki, N.; Suzuki, H.; Kurihara, H.; Sakashita, H.; Takeuchi, M.; Fujita, S.; Yamada, T.; Tanaka, A. Coumarin and chromen-4-one analogues as tautomerase inhibitors of macrophage migration inhibitory factor. Discovery and X-ray crystallography. *J. Med. Chem.* 2001, 44, 540-547.

Orita, M.; Yamamoto, S.; Katayama, N.; Fujita, S. Macrophage migration inhibitory factor and the discovery of tautomerase inhibitors. *Curr. Pharm. Des.* 2002, 8, 1297-1317.

Riedemann, N. C.; Guo, R. F.; Ward, P. A. Novel strategies for the treatment of sepsis. *Nat. Med.* 2003, 9, 517-524.

Roger, T.; David, J.; Glauser, M. P.; Calandra, T. MIF regulates innate immune responses through modulation of Toll-like receptor 4. *Nature* 2001, 414, 920-924.

Rosengren, E.; Bucala, R.; Aman, P.; Jacobsson, L.; Odh, G. et al. The immunoregulatory mediator macrophage migration inhibitory factor (MIF) catalyzes a tautomerization reaction. *Mol. Med.* 1996, 2, 143-149.

Senter, P. D.; Al-Abed, Y.; Metz, C. N.; Benigni, F.; Mitchell, R. A. et al. Inhibition of macrophage migration inhibitory factor (MIF) tautomerase and biological activities by acetaminophen metabolites. *Proc Natl Acad Sci USA* 2002, 99, 144-149

Sugimoto, H.; Suzuki, M.; Nakagawa, A.; Tanaka, I.; Fujinaga, M. et al. Crystallization of rat liver macrophage migration inhibitory factor for MAD analysis. *J. Stuct. Biol.* 1995, 115, 331-334.

Sun, B.; Nishihira, J. et al. Macrophage migration inhibitory factor promotes tumor invasion and metastasis via the Rho-dependent pathway. *Clin. Cancer Res.* 2005, 11, 1050-1058.

Sun, H. W.; Bernhagen, J.; Bucala, R.; Lolis, E. Crystal structure at 2.6-A resolution of human macrophage migration inhibitory factor. *Proc. Natl. Acad. Set. USA* 1996, 93, 5191-5196.

Suzuki, M.; Sugimoto, H.; Nakagawa, A.; Tanaka, I.; Nishihira, J. et al. Crystal structure of the macrophage migration inhibitory factor from rat liver. *Nat. Struct. Biol.* 1996, 3, 259-266.

Taylor, A. B.; Johnson, W. H., Jr.; Czerwinski. R. M.; Li, H. S.; Hackert, M. L. et al. Crystal structure of macrophage migration inhibitory factor complexed with (E)-2-fluoro-p-hydroxycinnamate at 1.8 A resolution: implications for enzymatic catalysis and inhibition. *Biochemistry* 1999, 38, 7444-7452.

Wang, H.; Bloom, O.; Zhang, M.; Vishnubhakat, J. M.; Ombrellino, M. et al. HMG-1 as a late mediator of endotoxin lethality in mice. *Science* 1999, 285, 248-251

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound of Formula I:

(i) wherein R1 is COOCH$_2$Ph or PhOMe, where Me is CH$_3$ and Ph is phenyl, and R2, R3, R4 and R5 are independently a halogen or H, wherein either (i) only one of R2, R3, R4 and R5 is not H, or (ii) R2, R3, R4 and R5 are H, or (ii) wherein R1 is COOCH$_2$PhOMe and R2, R3, R4 and R5 are independently a halogen or H, wherein only one of R2, R3, R4 and R5 is not H.

2. The compound of claim 1, wherein only one of R2, R3, R4 and R5 is not an H.

3. The compound of claim 2, wherein R2 is a halogen.

4. The compound of claim 2, wherein R2 is a fluoro group.

5. The compound of claim 1, wherein R1 is PhOMe.

6. The compound of claim 5, wherein R2 is a fluoro group, and R3, R4 and R5 are H.

7. The compound of claim 5, wherein R2 is a chloro group, and R3, R4 and R5 are H.

8. The compound of claim 5, wherein R2 is a bromo group, and R3, R4 and R5 are H.

9. The compound of claim 5, wherein R2, R3, R4 and R5 are H.

10. The compound of claim 1, wherein R2, R3, R4 and R5 are H.

11. The compound of claim 1, wherein R1 is COOCH$_2$Ph, or PhOMe, where Me is CH$_3$ and Ph is phenyl, and R2, R3, R4 and R5 are independently a halogen or H, wherein either (i) only one of R2, R3, R4 and R5 is not H, or (ii) R2, R3, R4 and R5 are H.

* * * * *